United States Patent
Husmark et al.

(10) Patent No.: US 9,125,768 B2
(45) Date of Patent: *Sep. 8, 2015

(54) HYGIENE TISSUE COMPRISING A MICROBE-INHIBITING COMPOSITION

(75) Inventors: Ulrika Husmark, Mölnlycke (SE); Ulla Forsgren Brusk, Pixbo (SE)

(73) Assignee: SCA HYGIENE PRODUCTS AB, Gothenburg (SE)

( * ) Notice: Subject to any disclaimer, the term of this patent is extended or adjusted under 35 U.S.C. 154(b) by 913 days.

This patent is subject to a terminal disclaimer.

(21) Appl. No.: 12/514,851

(22) PCT Filed: Nov. 17, 2006

(86) PCT No.: PCT/SE2006/001312
§ 371 (c)(1),
(2), (4) Date: May 14, 2009

(87) PCT Pub. No.: WO2008/060199
PCT Pub. Date: May 22, 2008

(65) Prior Publication Data
US 2010/0040673 A1 Feb. 18, 2010

(51) Int. Cl.
*A61L 15/46* (2006.01)
*A47K 10/16* (2006.01)
*A61F 13/15* (2006.01)
(Continued)

(52) U.S. Cl.
CPC ............... *A61F 13/15* (2013.01); *A61L 15/20* (2013.01); *A61L 15/40* (2013.01); *A61L 15/46* (2013.01); *A61L 15/36* (2013.01); *A61L 2300/21* (2013.01); *A61L 2300/214* (2013.01); *A61L 2300/30* (2013.01); *A61L 2300/404* (2013.01); *A61L 2300/45* (2013.01)

(58) Field of Classification Search
CPC ........ A47K 10/16; A61L 15/46; A61L 15/20; A61L 15/40; A61L 2300/21; A61L 2300/30; A61L 2300/45; A61L 2300/214; A61F 13/15
See application file for complete search history.

(56) References Cited

U.S. PATENT DOCUMENTS 5,762,948 A * 6/1998 Blackburn et al. ............ 424/404
6,110,908 A * 8/2000 Guthery ........................ 514/188
(Continued)

FOREIGN PATENT DOCUMENTS

CN 1787841 A 6/2006
EP 1060240 A1 12/2000
(Continued)

OTHER PUBLICATIONS

Beuchat, Applied and Environmental Microbiology, 39(6), pp. 1178-1182 (1980).*
(Continued)

*Primary Examiner* — Rachael E Bredefeld
*Assistant Examiner* — Lisbeth C Robinson
(74) *Attorney, Agent, or Firm* — Buchanan Ingersoll & Rooney PC

(57) ABSTRACT

A hygiene tissue (1), such as a wet wipe, dry wipe, washcloth, patch, towelette, napkin, and the like includes a microbe-inhibiting composition (8). The microbe-inhibiting composition (8) includes an extracellular product of at least one probiotic bacterium and at least one additive in the form of an organic acid, with at least one of its pKa value not exceeding 5.5, and/or a salt thereof.

11 Claims, 6 Drawing Sheets

(51) Int. Cl.
  *A61L 15/36* (2006.01)
  *A61L 15/20* (2006.01)
  *A61L 15/40* (2006.01)

(56) References Cited

U.S. PATENT DOCUMENTS

| | | | | |
|---|---|---|---|---|
| 6,277,374 | B1* | 8/2001 | Vandenbergh et al. | 424/115 |
| 6,531,126 | B2* | 3/2003 | Farmer | 424/115 |
| 6,716,435 | B1 | 4/2004 | Farmer et al. | |
| 6,761,885 | B1 | 7/2004 | Hakansson et al. | |
| 7,482,023 | B2* | 1/2009 | Runeman et al. | 424/484 |
| 2001/0033838 | A1 | 10/2001 | Farmer | |
| 2002/0044926 | A1 | 4/2002 | Reid et al. | |
| 2002/0090365 | A1 | 7/2002 | Chrisope | |
| 2003/0143262 | A1* | 7/2003 | Brusk et al. | 424/443 |
| 2004/0142832 | A1* | 7/2004 | Runeman et al. | 510/130 |
| 2004/0241151 | A1 | 12/2004 | Husmark et al. | |
| 2004/0243076 | A1* | 12/2004 | Husmark et al. | 604/358 |
| 2005/0176613 | A1* | 8/2005 | Wai Cheung et al. | 510/383 |
| 2005/0276836 | A1 | 12/2005 | Wilson et al. | |
| 2006/0062774 | A1* | 3/2006 | Davis et al. | 424/93.45 |
| 2006/0171936 | A1 | 8/2006 | Gueniche et al. | |
| 2006/0177429 | A1 | 8/2006 | Farmer et al. | |
| 2010/0030172 | A1 | 2/2010 | Husmark et al. | |
| 2010/0069860 | A1 | 3/2010 | Brusk et al. | |
| 2010/0136210 | A1* | 6/2010 | Forsgren-Brusk et al. | 427/2.3 |

FOREIGN PATENT DOCUMENTS

| | | |
|---|---|---|
| EP | 1140226 B1 | 3/2006 |
| GB | 2112285 A * | 7/1983 |
| RU | 2212902 C2 | 9/2003 |
| WO | WO 92/13577 A1 | 8/1992 |
| WO | WO 94/23585 A1 | 10/1994 |
| WO | WO 97/02846 A1 | 1/1997 |
| WO | WO 98/46261 A1 | 10/1998 |
| WO | WO 99/17788 A1 | 4/1999 |
| WO | WO 99/17813 A1 | 4/1999 |
| WO | WO 99/45099 A1 | 9/1999 |
| WO | WO 99/45976 | 9/1999 |
| WO | WO 00/35502 A1 | 6/2000 |
| WO | WO 00/61201 A1 | 10/2000 |
| WO | WO 00/76878 A1 | 12/2000 |
| WO | WO 02/28446 A1 | 4/2002 |
| WO | WO 03/038068 | 5/2003 |
| WO | WO 2004/022727 | 3/2004 |
| WO | WO 2004/060416 A1 | 7/2004 |
| WO | WO 2004/101008 A1 | 11/2004 |
| WO | WO 2005034970 A1 * | 4/2005 |
| WO | WO 2005/086870 A2 | 9/2005 |
| WO | WO 2006114061 A1 * | 11/2006 |
| WO | WO 2008/060199 A1 | 5/2008 |
| WO | WO 2008/060200 A1 | 5/2008 |

OTHER PUBLICATIONS

Stiles et al., Journal of Food Protection, 65: 1188-1191 (2002).*
Moon, Journal of Applied Bacteriology, 55: 453-460 (1983).*
de Man et al., Journal of Applied Bacteriology, 23: 130-135 (1960).*
Heriban et al., Letters in Applied Microbiology, 16: 243-246 (1993).*
Mishra et al., Asia Pacific J Clin Nutr, 5: 20-24 (1996).*
Narendranath et al., Journal of Industrial Microbiology & Biotechnology 36: 171-177 (2001).*
Silva et al., Antimicrobial Agents and Chemotherapy, 31(8): 1231-1233 (1987).*
Lee et al., Journal of Microbiological Methods, 45:1-6 (2001).*
Corsetti et al., Appl. Microbiol. Biotechnol, 50: 553-256 (1998).*
Russian Federation Office Action dated Apr. 27, 2010 in foreign Application No. 2009122992/15(031913); and translation thereof.
International Search Report (PCT/ISA/210) completed for PCT/SE2006/001312, Jun. 28, 2007.
Written Opinion (PCT/ISA/237), completed for PCT/SE2006/001312, Jun. 28, 2007.
Written Opinion of Int'l Preliminary Exam Authority, completed for PCT/SE2006/001312, Jan. 27, 2009.
G.B. Hill et al., Bacteriology of the Vagina, 1984, p. 23-29.
B. Runeman et al., Experimental *Candida albicans* Lesions in Healthy Humans: Dependence on Skin pH, Acta Derm Veneroel 2000, 421-424.
U.S. Appl. No. 12/515,252, filed May 2009, Brusk et al.
Falagas et al., "Probiotics for Prevention of Recurrent Vulvovaginal Candidiasis a Review" Journal of Antimicrobial Chemotherapy, 2006, vol. 58, pp. 266-272.
Hooton et al., "*Escherichia coil* Bacteriuria and Contraceptive Method" JAMA, 1991, vol. 265, No. 1, pp. 64-69.
Redondo-Lopez et al., "Emerging Role of Lactobacilli in the Control and Maintenance of the Vaginal Bacterial Microflora" Reviews of Infectious Diseases, 1990, vol. 12, No. 5, pp. 856-872.
Strus et al., "Dzialanie In Vitro Bakterii Z Rodzaju *Lactobacillus* Izolowanych Z Pochwy Na Grzybywywolujace Kandydoze Sromu I Pochwy" Med. Dośw. Mikrobiol., 2005, vol. 57, pp. 7-17, in Russian with English Abstract.
Rönnqvist, "Inhibition of *Candida albicans* and *Candida glabrata* by two *Lactobacillus fermentum* Strains" Essum AB, 2008, 11 pages.
International Search Report and the Written Opinion of the International Search Authority Forms (PCT/ISA/210 and PCT/ISA/237) issued in corresponding International Application No. PCT/SE2006/001311 dated Jul. 6, 2007.
Notification of Receipt of Record Form (PCT/IB/301) issued in corresponding International Application No. PCT/SE2006/001311 dated Dec. 14, 2006.
International Search Report and the Written Opinion of the International Searching Authority Forms (PCT/ISA/210 and PCT/ISA/237) issued in corresponding International Application No. PCT/SE2006/001313 dated Jun. 29, 2007.
Written Opinion of the International Preliminary Examining Authority Form (PCT/IPEA/408) issued in corresponding International Application No. PCT/SE2006/001313 dated Jan. 27, 2009.
Notification of Receipt of Record Form (PCT/IB/301) issued in corresponding International Application No. PCT/SE2006/001313 dated Jan. 4, 2007.
Maidak et al., "A New Version of the RDP (Ribosomal Database Project)" Nucleic Acids Research, 1999, vol. 27, No. 1, pp. 171-173.
Rainey et al., "The Genus *Nocardiopsis* Represents a Phylogenetically Coherent Taxon and a Distinct Actinomycete Lineage: Proposal of *Nocardiopsaceae* fam. nov." International Journal of Systematic Bacteriology, 1996, vol. 46, No. 4, pp. 1088-1092.
Copending U.S. Appl. No. 12/514,909, filed May 14, 2009 by Ulrika Husmark et al.
Official Action issued on Jun. 9, 2011 by the Chinese Patent Office in corresponding Chinese Patent Application No. 200680056409.9.
D. Rönnqvist et al., "*Lactobacillus fermentum* Ess-1 with unique growth inhibition of vulvo-vaginal candidiasis pathogens" *Journal of Medical Microbiology*, 2007, pp. 1500-1504, vol. 56.
D. Rönnqvist et al. "Selection and characterization of a *Lactobacillus plantarum* strain promising as a urogenital probiotic," *Microbial Ecology in Health and Disease*, 2005, pp. 75-82, vol. 17.
Cabo, M.L. et al."Apparent Antifungal Activity of Several Lactic Acid Bacteria against Penicillium Discolor is Due to Acetic Acid in the Medium," Journal of Food Protection 2002, 65(8), 1309-1316.
Office Action issued on Jan. 13, 2015, by the Brazilian Patent Office in corresponding Brazilian Patent Application No. PI0622146-7, and a partial English Translation of the Office Action. (9 pages).

* cited by examiner

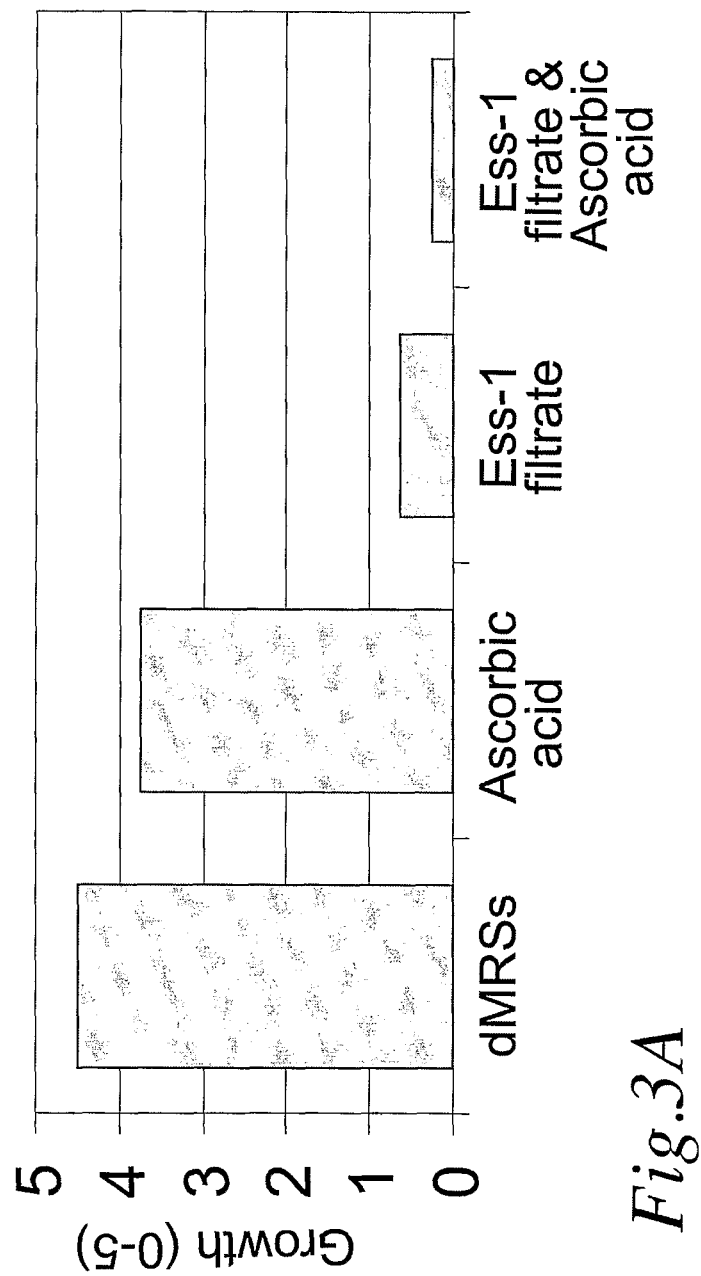

HYGIENE TISSUE COMPRISING A MICROBE-INHIBITING COMPOSITION

TECHNICAL FIELD

The present invention relates to a hygiene tissue, such as a wet wipe, dry wipe, washcloth, patch, towelette, napkin, or the like, that comprises at least one extracellular product of at least one probiotic bacterium and at least one of the selected additives giving a synergistic inhibitory effect on *Candida albicans* or other unwanted microorganisms.

BACKGROUND OF THE INVENTION

The urogenital area harbors a complex microbial ecosystem comprising more than 50 different bacterial species (Hill et al., Scand. J. Urol. Nephrol. 1984; 86 (suppl.) 23-29). The dominating species for fertile women in this area are lactic acid producing bacteria belonging to the genus *Lactobacillus*. These lactic acid producing members are important for retaining a healthy microbial flora in these areas, and act as probiotic bacteria with an antagonistic effect against pathogenic microbial species. Lactic acid producing bacteria inhibit growth and colonization by other microorganisms by occupying suitable niches for colonization, by forming biofilms and competing for available nutrients, thereby excluding colonization by harmful microorganisms. Also, the production of hydrogen peroxide, specific inhibiting substances, such as bacteriocines, and organic acids (including lactic acid and acetic acid) that lower the pH, inhibit the growth and colonization by other microorganisms.

The microbial ecosystem of a healthy individual can be disturbed by the use of antibiotics, during hormonal changes, such as during pregnancy or use of contraceptives with estrogen, during menstruation, after menopause, in people suffering from diabetes etc. Also, microorganisms may spread from the anus to the urogenital area, this results in a disturbance of the normal microbial flora and leaves the individual susceptible to microbial infections such as vaginitis, *candida* infections, urinary tract infections and skin infections. Microorganisms commonly associated with these kinds of infections belong to the genera *Escherichia, Enterococcus, Pseudomonas, Proteus, Klebsiella, Streptococcus, Staphylococcus, Gardnerella* and *Candida*. Women are at particular risk due to their shorter distance between the anus and the urogenital tract; specially at risk are young women, who not yet have a well developed microflora in the urogenital area and older women, who in most cases no longer have a protective flora.

Similarly to the urogenital area, the skin is colonized by an array of organisms, which forms its normal flora. The numbers and identity of the organisms vary between different skin sites. This, together with the skin's structural barrier, provides the host with an excellent defense against invading microbes. The number of bacteria on the skin varies from a few hundred per $cm^2$ on the arid surfaces of the forearm and back, to tens of thousands per $cm^2$ on the moist areas such as the axilla and groin. This normal flora plays an important role in preventing foreign organisms from colonizing the skin, but it to needs to be kept in check, in order to avoid skin infections.

*Staphylococcus aureus* is the most common cause of minor skin infections, such as boils or abscesses, as well as more serious post-operative wound infection. Treatment involves drainage and this is usually sufficient for minor lesions, but antibiotics may be given in addition when the infection is severe and the patient has fever.

Toxic shock syndrome is a systemic infection caused by *S. aureus* strains which produce toxic shock syndrome toxin. The disease came to prominence through its association with tampon use by healthy women, but it is not confined to women and can occur as a result of *S. aureus* infection at non-genital sites.

Other common skin infections are caused by *Streptococcus pyogenes* (group A streptococci). The organisms are acquired through contact with other people with infected skin lesions and may first colonize and multiply on normal skin prior to invasion through minor breaks of the epithelium and the development of lesions.

Treatment with penicillin or erythromycin may be necessary to combat the infection.

*Candida* likes skin sites which are moist and warm and also rapidly colonizes damaged skin. Hence, the relative dryness of most areas of skin prevents the growth of *Candida*, which therefore are found in low numbers on healthy skin. *Candida* also colonizes the oral and vaginal mucosa and over-growth may result in disease in these sites. *C. albicans* is associated with diaper dermatitis. A study has shown that *C. albicans* induced lesions are remarkably influenced by pH, a lower skin pH giving less lesions (B. Runeman, Acta Derm Venereol 2000; 80: 421-424).

One way to reduce the problems with the kind of infections described above is to have a good personal hygiene. However, excessive use of cleaning agents not only decreases the amount of harmful microbes, but can harm the beneficial microbial flora, again render it susceptible for pathogenic species to colonize and cause infections. Alternatively, administration of lactic acid producing bacteria to the urogenital area and the skin, in order to out-compete pathogenic species and facilitate reestablishment and maintenance of a beneficial microbial flora in these areas, has been found to be a successful means to treat and prevent microbial infections It has been suggested that lactic acid producing bacteria can be delivered via a absorbent products, such as diapers, sanitary napkin, incontinence guards, panty liners and tampons, as described in, for example, WO 92/13577, WO 97/02846, WO 99/17813, WO 99/45099 and WO 00/35502. However, absorbent articles may not always be an optimal administration route, since carrying of an absorbent article often is apprehended as uncomfortable, indiscrete and warm. This administration route can also be inconvenient as repeated administration of lactic acid producing bacteria is often necessary to retain the efficacy of the treatment or the preventative effect. Also, these products cannot be used for delivery of the bacteria to other regions of the body than the urogenital area. Therefore, for some applications it can be more convenient to administer lactic acid producing bacteria by other means than absorbent products. A second problem with the administration of lactic acid producing bacteria via absorbent articles relates to the manufacturing of such products, since all possible variants and sizes of the product have to be supplied with the bacteria. Therefore the administration via a product that could be used without individual adjustments could provide a manufacturing advantage over the absorbent products.

It has also been suggested to delivering the lactic acid producing bacteria via hygiene tissue that allows both cleaning and caring of the skin and urogenital area and delivery of probiotic lactic acid producing bacteria, for example, WO 04/060416.

A major problem with providing products intended to be used for transfer of lactic acid producing bacteria, is that the bacteria have to retain viability during transport and storage of the products. Lactic acid producing bacteria rapidly lose viability under semi-moist conditions, and it is therefore important that the bacteria are not exposed to moisture during storage. One way to partly overcome this problem in absorbent products provided with lactic acid producing bacteria has been to supply the products with the bacteria, drying said products to remove most of the moisture in them and providing the product in moisture impervious packages (WO99/17813).

WO 00/61201 discloses a sanitary product containing an effective amount of a viable, non-pathogenic, probiotic bacteria, such as *Bacillus coagulans*, or an extracellular product thereof.

EP 1140226 describes the combination of a pH regulating substance in the form of a partially neutralized superabsorbent material with lactic acid-producing bacteria.

In view of the prior art there is still a need for hygiene tissues with an improved prebiotic and/or probiotic effect, which hygiene tissues are easy to store and transport.

SUMMARY OF THE INVENTION

In view of this prior art it is an object of the present invention to provide a hygiene tissue comprising a microbe-inhibiting composition with an enhanced effect. It is also an object of the present invention that said hygiene tissue comprising a microbe-inhibiting composition easily transported and stored without the microbe-inhibiting composition losing its microflora balancing and health promoting function The above defined problems are solved by the present invention by a hygiene tissue such as a wet wipe, dry wipe, washcloth, patch, towelette, napkin, and the like comprising a microbe-inhibiting composition comprising an extracellular product of at least one probiotic bacterium and at least one additive in the form of an organic acid, having a pKa value not exceeding 5.5, and/or a salt thereof, giving a synergistic prebiotic effect.

In one aspect said pKa value do not exceed 5.

According to the present invention said microbe-inhibiting extracellular product is a supernatant obtained by filtration or centrifugation of a culture of a probiotic bacterium.

In one embodiment said microbe-inhibiting composition is substantially free from probiotic bacteria, the probiotic bacteria are preferably not present in an amount higher than 100 CFU/ml and more preferably not higher than 10 CFU/ml.

In one embodiment of the invention said microbe-inhibiting composition comprises at least one probiotic bacterium, an extracellular product of at least one probiotic bacterium and at least one of said additives.

In one aspect of the invention the probiotic bacterium is a lactic acid producing bacterium.

In a further aspect of the invention the lactic acid producing bacterium is *Lactobacillus plantarium* LB 931. In one other aspect of the invention the lactic acid producing bacterium is *Lactobacillus fermentum* Ess-1. In a further aspect of the invention the lactic acid producing bacterium is a combination of *Lactobacillus plantarum* LB 931 and *Lactobacillus fermentum* Ess-1.

In one aspect of the invention said additive is chosen from acetic acid, propionic acid, lactic acid, ascorbic acid, phenylalanine, citric acid, butyric acid, valeric acid, capronic acid, succinic acid and/or a salt thereof. Preferably said additive is chosen from acetic acid, propionic acid, lactic acid, phenylalanine, citric acid or succinic acid, ascorbic acid, and/or a salt thereof. Most preferably said additive is chosen from ascorbic acid, acetic acid, propionic acid, succinic acid and/or a salt thereof.

In another aspect of the invention said salt is a sodiumsalt; preferably sodium propionate or sodium acetate.

Since the microbe inhibiting composition of the invention combining an extracellular of a probiotic bacterium and an additive gives an unexpected synergistic effect in inhibition of pathogenic microorganisms, a hygiene tissue according to the invention comprising this microbe inhibiting composition has an enhanced prebiotic effect. In addition a hygiene tissue of the present invention is easy to transport and store without the microbe inhibiting composition losing its beneficial properties.

DESCRIPTION OF THE DRAWINGS

FIG. 3a. shows the growth of *Candida albicans* when extracellular product of the *Lactobacillus fermentum* Ess-1 was combined with the additive ascorbic acid.

DEFINITIONS

Figure 1:
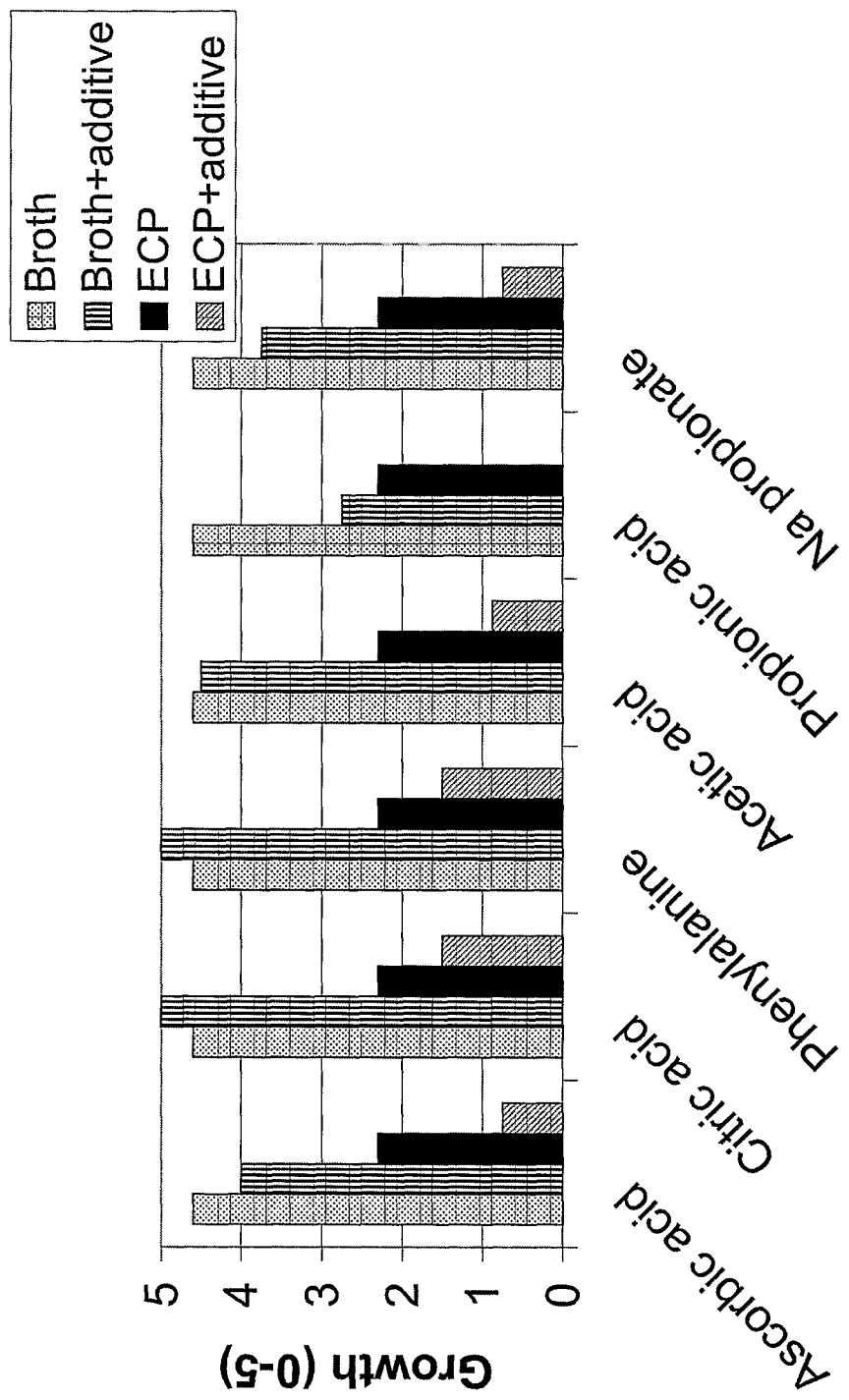
FIG. 1. shows the growth of *C. albicans* in extracellular product of LB 931 with addition (50 mM) of different acids/salts.

Probiotics/probiotic in the present context relates to live microorganisms that confer a health benefit when administered in adequate amounts to a host.

By lactic acid producing bacteria is meant bacterium producing lactic acid. Preferred lactic acid producing bacteria for the object of the present invention include bacteria from the genera *Lactobacillus, Lactococcus* and *Pediococcus*. Preferably the selected bacterium used is from the species *Lactococcus lactis, Lactobacillus fermentum, Lactobacillus rhamnosus, Lactobacillus acidophilus* or *Lactobacillus plantarum*. More preferably the bacterial strain is selected from *Lactobacillus plantarum* or *Lactobacillus fermentum*. Even more preferably the lactic acid producing bacterium is *Lactobacillus plantarum* 931 (deposition No. (DSMZ): DSM 11918) and *Lactobacillus fermentum* Ess-1 (deposition No. (DSMZ): DSM 17851).

Prebiotics/prebiotic in the present contexts relates to substances that promote a balanced micro flora when administered in adequate amounts to a host. Examples are nutrients for probiotic bacteria, substances that promote adhesion to the host for probiotic bacteria, pH-regulating substances and extracellular products from probiotic bacteria.

By microbe-inhibiting is meant the inhibition of growth, colonization and/or survival of other microorganisms.

By extracellular product is meant products secreted in cultures of probiotic bacteria which extracellular products have an antimicrobial effect. The extracellular product is obtained from the bacterial cell cultures by e.g. filtration, centrifugation, or both of these, and the resulting supernatant comprising the extracellular product possesses antimicrobial activity useful in a microbe-inhibiting composition.

By "hygiene tissue" is meant any device for wiping, cleaning and caring of the skin and the urogenital area which also can be used to deliver a microbe-inhibiting composition to these areas, for instance a wet wipe, dry wipe, washcloth, patch, towelette, napkin, and the like.

By lipid is in the present context meant substances that are insoluble in water but soluble in an organic solvent.

DETAILED DESCRIPTION

An object of the present invention is to provide hygiene tissues, suitable for wiping, cleaning and caring of the skin and the urogenital area and simultaneously release a microbe-inhibiting composition that is to be transferred to the skin The present invention pertains to solve the problem of growth, colonization and/or survival of pathogenic microorganisms in the urogential area and on the skin by using said hygiene tissue. This problem is in the present invention solved by applying a microbe-inhibiting composition comprising an extracellular product of at least one probiotic bacterium and at least one additive, in the form of an organic acid, having a pKa value not exceeding 5.5 and/or a salt thereof, to a hygiene tissue.

By combining said additive with said extracellular product a surprisingly large increase in the inhibition of *Candida albicans* and several other microorganism such as for example *E. coli* and *S. Saprofyticus* is obtained.

It should be noted that of course a combination of two or more probiotic bacterial strains may be used to produce the extracellular product of the invention. Also it is of course possible to use a combination of at least two bacterial strains in a microbe-inhibiting composition of the invention.

Figure 4:
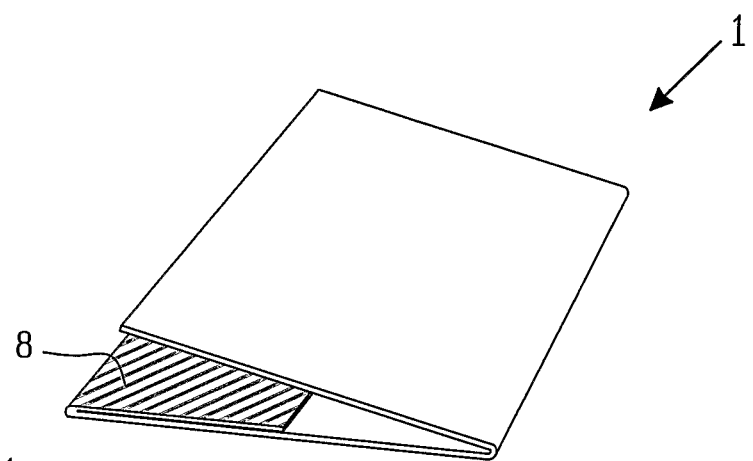
FIG. 4-6 show perspective views of hygiene tissues according to the present invention.
Figure 5:
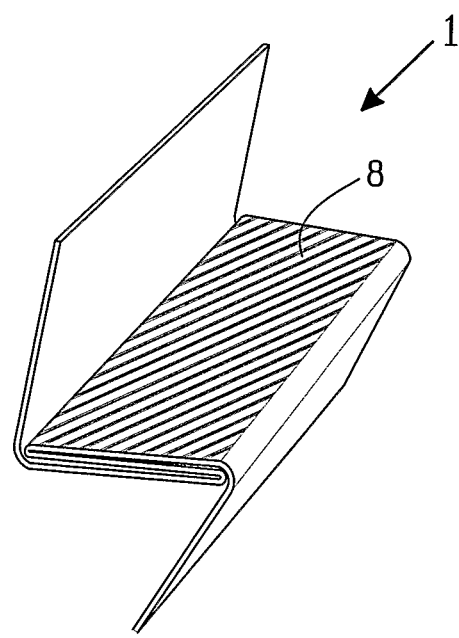
Figure 6:
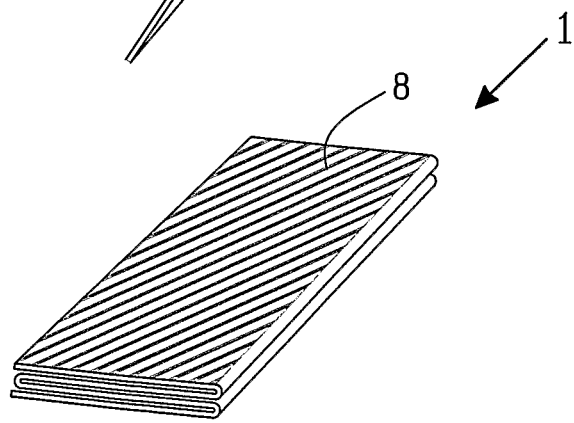

FIG. 4 to 6 shows preferred embodiments of a hygiene tissue 1 containing the microbe-inhibiting composition 8. The hygiene tissue 1 provided can be composed of a matrix comprising any natural or synthetic fiber, such as rayon, cellulose, regenerated cellulose, polyester, polyolefine fibers, textile and the like, or foam, nonwoven, felt or batting, or combinations thereof.

It is understood that the hygiene tissue described above and shown in the drawings only represents non-limiting examples and that the present invention is not limited thereto, but can be used in any type of hygiene tissues as defined above.

In one embodiment of the present invention when the microbe-inhibiting composition comprises said extracellular product and said additive, said composition is substantially free from probiotic bacteria. It is noted that it is extremely difficult to manufacture a composition that is totally free from probiotic bacteria, therefore it is preferably not present in an amount higher than 100 CFU/ml and preferably not higher than 10 CFU/ml. This composition has the advantage of less stringent storage requirements since the extracellular product is more durable than the live microorganism.

In another embodiment of the invention said microbe-inhibiting composition comprises at least one probiotic bacterium, an extracellular product of at least one probiotic bacterium and at least one of said additives. In this embodiment when said microbe-inhibiting composition also comprises at least one probiotic bacteria the effect is said to be prebiotic and probiotic.

The probiotic bacteria which are suitable for use in the present invention produce in most cases acid and are in all cases non-pathogenic. There are many suitable bacteria identified herein below, although the invention is not limited to currently known bacterial species and strains as long as the above function and the objectives of the probiotic bacteria are fulfilled.

An important characteristic of the probiotic lactic acid producing bacteria is their capability to produce lactic acid and in some cases also other acids, said acids increases the acidity of the skin mucosa which helps in preventing the growth, colonization and survival of undesired fungi and bacteria. Thus, by the mechanism of acid production, these probiotic bacteria inhibit the growth of competing and harmful bacteria and fungi. Further important characteristics of said bacteria is their ability to produce hydrogen peroxide and other microbe inhibiting substances and also their ability to adhere to cell surfaces and thereby prevent adhesion of other harmful bacteria and fungi to these surfaces.

Typical lactic acid-producing bacteria useful in a microbe-inhibiting composition of this invention are all members of the *Lactobacillus*, *Lactococcus* or *Pediococcus*, which are efficient acid producers, and also including non-pathogenic members of the *Bacillus* genus, all members of the *Bifidobacterium* genus, and *Pseudomonas limbergii*, although certain species are especially preferred as described below.

Preferred members of the *Lactobacillus* genus include *Lactobacillus acidophilus*, *Lactobacillus bulgaricus*, *Lactobacillus casei*, *Lactobacillus cereale*, *Lactobacillus delbrukeii*, *Lactobacillus fermentum*, *Lactobacillus gaserii*, *Lactobacillus jensenii*, *Lactobacillus plantarum*, *Lactobacillus rhamnosus*, *Lactobacillus salivarius*, *Lactobacillus thermophilus*, *Lactobacillus paracasai sp. paracasai*, *Lactobacillus crispatus*, *Lactobacillus helveticus*, *Lactobacillus lactis*, and the like.

Particularly preferred is the novel bacterium *Lactobacillus fermentum* Ess-1 and *Lactobacillus plantarum* LB 931. LB 931 has previously been found valuable for preventing and/or treating urogenital infections as it inhibits growth of a large number of pathogenic microorganisms, in e.g. EP1060240. *Lactobacillus fermentum* Ess-1 (deposition No. (DSMZ): DSM 17851) was deposited according to the Budapest Treaty at Deutsche Sammlung von Mikroorganismen und Zellkulturen GmbH (Mascheroder Weg 1 b, D-38124 Braunschweig) (depositor Essum AB, Box 3160, SE 90304 Umeå, Sweden, deposited on Jan. 6, 2006).

It should be noted that although in the examples below where only two Lactobacilli strains have been used, these bacterial strains should only be seen as a model for probiotic bacteria useful in the practice of the present invention. Therefore the below examples should not be seen as limiting for the present invention. It is intended that any lactic acid producing species of probiotic bacteria may be used in the composition.

The extracellular product of the present invention is obtained from a bacterial culture. Bacteria suitable for the present invention secrete products having antimicrobial activity which is useful for the objectives of the present invention. In order to obtain the extracellular products, cell cultures are harvested as described below and the supernatant is obtained by centrifugation or filtration or both. The thus obtained supernatant has a microbe inhibiting activity due to extracellular products comprised therein. An example of how the extracellular product may be prepared is described under Example 3.

The extracellular product may be in the form as when obtained directly from a bacterial culture but it is also possible to concentrate and/or purify the supernatant further. By purification is meant that some of the microbe-inhibiting substances are isolated by for example chromatography, crystallisation or distillation and used separately or in combination with other isolated substances.

The additive which is added to the probiotic bacteria and/or to the extracellular product in the present invention is in the form of an organic acid or a salt thereof. When choosing said additive this should of course be made from a product safety point of view. The organic acids or the corresponding salts should be of such nature that when applying them onto a sanitary article they should not cause any skin irritation to the user of the hygiene tissue, therefore the pKa of the organic acid, when the measurement are performed in water at 25° C., should preferably not be lower than 2. If the pKa values instead are too high, the organic acids or the salts thereof will mainly be in their acid forms. This means that the additive will not be sufficiently dissociated into a hydrogen ion and its deprotonated, anionic form, which is believed to be a prerequisite in order to obtain said synergistic microbe-inhibiting effect with the probiotic bacterium and/or the extracellular product thereof. Therefore the pKa value for the organic acid suitable for the present invention should be lower than 5.5, preferably lower than 5. If the organic acid suitable for the present invention have more than one pKa value, at least one of these values should be lower than 5.5, preferably lower than 5.

When the extracellular product is in the form of a supernatant, the solubility of these organic acids or the corresponding salts should be sufficiently high so that said additive can be dissolved in the supernatant.

In a preferred embodiment of the present invention the additive is chosen from acetic acid, propionic acid, lactic acid, ascorbic acid, phenylalanine, citric acid, butyric acid, valeric acid, capronic acid, succinic acid and/or a salt thereof. Preferably said additive is chosen from acetic acid, propionic acid, lactic acid, ascorbic acid, phenylalanine, citric acid or succinic acid, and/or a salt thereof. Most preferably said additive is chosen from ascorbic acid, acetic acid, propionic acid, succinic acid and/or a salt thereof.

In one embodiment of the invention the salt is a sodium salt. Especially preferred salts are sodium propionate and sodium acetate.

The product typically comprise about 0.5-100 ml and preferably contains 1-10 ml of the extracellular product.

Said additive is typically added with a final concentration of 5-100 mM to the extracellular product.

If the hygiene tissue further comprises probiotic bacteria, these are typically provided in amounts of about $10^6$-$10^{11}$ CFU of viable probiotic bacteria per hygiene tissue. Typically the bacteria are in the form of cells or spores which are provided in a suspension.

These amounts can however vary depending on the specific application, product formulation and intended use.

The microbe-inhibiting composition may be directly applied to the hygiene according to the invention or provided in a pharmaceutically acceptable carrier which may enhance the transfer of the microbe-inhibiting composition, examples of such includes lipids. Examples of lipids suitable for the present invention include petroleum derived lipids, such as paraffinum liquidum (mineral oils, paraffin oils, and vaseline oils), petrolatum (vaseline and petroleum jelly), cera microcrystallina, ozokerite, ceresine and paraffins. Alternatively, synthetic lipids, such as dimethicone, cyclomethicone and silicone esters, such ascetearyl methicone can be used. A third alternative is to use animal- or plant-derived lipids, which usually are triglycerides.

In one preferred embodiment the microbe inhibiting composition is in the form of a suspension, said suspension may be applied directly to the sanitary article by impregnation, spraying, printing or the like, whereafter the hygiene tissue may be dried, by for e.g. heat drying.

In another preferred embodiment the microbe-inhibiting composition is in the form of a powder. The powder may be mixed into said pharmaceutically acceptable carrier or be directly applied to the hygiene tissue as a powder. In the case where the powder is mixed into a pharmaceutically acceptable carrier, this mixture may be applied to the hygiene tissue by impregnation, spraying, printing or the like, whereafter the hygiene tissue may be dried. A delivery device, meaning a separate pocket attached to the hygiene tissue is also a possible way of deliver said microbe-inhibiting composition.

The powder according to the above may be obtained by evaporating the above discussed suspension such as by heat drying, convective drying, spray drying, freeze drying, or the like. It may be necessary to further mould the dried microbe-inhibiting composition in order to obtain a fine powder. The probiotic bacteria are preferably freeze dried.

In one preferred embodiment the hygiene tissue may be a dry hygiene tissue, meaning that the hygiene tissue either comprises the microbe-inhibiting composition as a powder or that the hygiene tissue has been dried after the application of the suspension containing the microbe-inhibiting composition. In this case the hygiene tissue is intended to be wetted before use and the solubility of the additive should therefore be of such nature that the additive rapidly comes into solution when contacted by for e.g. water.

In a further preferred embodiment the hygiene tissue may be a wet hygiene tissue, meaning for e.g. that the hygiene tissue is impregnated with either the above suspension or the pharmaceutically acceptable carrier comprising the microbe-inhibiting composition.

When the hygiene tissue comprises live probiotic bacteria the bacteria must be protected from moisture. The sanitary article may therefore be hermetically enclosed in a moisture-impervious package. WO 00/76878 gives an example of such a moisture impervious package. Another example of how the bacteria can be protected is by the use of a delivery system as exemplified in for example WO 02/28446.

The present invention also aims to decrease the problems with retaining the effect during storage. Since all the effect in some embodiments and at least parts of the effect in other embodiments comes from a composition containing substantially no living organisms, the problem of keeping the microorganism viable and thus functional is eliminated.

The prior art discloses absorbent articles only comprising probiotic bacteria or extracellular products thereof. However the microbial inhibiting effect, especially against *Candida* and the transfer of the probiotic bacteria from the sanitary article to the wearer, is not always completely satisfying, there are also many problems to overcome when producing and storing sanitary products containing viable microorganism One advantageous way of providing the hygiene tissue according to the present invention is therefore as a kit together with an absorbent article. Regular use of absorbent article has an impact on the uro-genital microclimate, which may lead to an imbalance in the urogenital microflora. The addition of a microbe-inhibiting composition may improve this balance. Since regular users of absorbent articles may be at extra risk and since changing of the absorbent article occurs at regular times this could be an effective way of reaching a target group and establishing a routine for administrating the microbe-inhibiting composition.

Another possibility is to deliver said microbe-inhibiting composition separately in a form which is convenient to apply directly to a hygiene tissue by the user, for example in its liquid form, as a powder, dispersed in a lotion, dispersed in oil. The supply means for said microbe-inhibiting composition could be a spray, a roll-on device, a tube, a bottle, an ampoule, a strip or a stick.

In a still further aspect of the invention the microbe-inhibiting composition is used in combination with the hygiene tissue according to the invention.

Another aspect of the invention is to preparing a hygiene tissue comprising applying said microbe-inhibiting composition to said hygiene tissue.

Experimental Section
Test 1

The purpose of this test was to determine whether selected additives affect the growth of *Candida albicans* and if an improved growth inhibition can be achieved when they are added to the extracellular products of *Lactobacillus plantarum*, LB 931. The additives used in this test were ascorbic acid, citric acid, phenylalanine, acetic acid, propionic acid and sodium propionate.

Method

Yeast Strain

A clinical isolate of *Candida albicans* (designated *C. albicans* 702) was used as test strain. It was isolated from the vagina of a woman with vaginal candidiasis.

Control

As control pure dMRSs broth (MRS broth without addition of sodium acetate) was used. A specified volume was transferred to wells of a micro titre plate and was let to air dry (45° C. minimum of 20 hrs).

Extracellular Product (ECP)

Cultures of LB 931 grown in dMRSs broth were centrifuged to pellet the cells and sterile filtered using a 0,22 µm filter (MILLIPORE filter, Bedford, USA) in order to obtain the LB 931 supernatant comprising the LB 931 extracellWar product. A specified volume of sterile filtered supernatant was transferred to wells of a micro titre plate and was let to air dry (45° C. minimum of 20 hrs) and thereafter resuspended in steril e distilled water to a concentration three times higher and 200 µl were transferred to 96-wells micro titre plates.

Extracellular Product with Additive

The additives were added to a final concentration of 50 mM to tubes containing the sterile filtered supernatant of LB 931. A specified volume was transferred to wells of a micro titre plate and was let to air dry (45° C. minimum of 20 hrs) and thereafter resuspended in sterile distilled water to a concentration three times higher (i.e. the volume of the sterile distilled water is about one third of the specified volume before air drying) and 200 µl were transferred to 96-wells micro titre plates.

Broth with Additive

The additives were added to a final concentration of 50 mM in dMRSs broth. pH was adjusted to the same pH-value as in the extracellular product with additive for the respective additive. A specified volume was transferred to wells of a micro titre plate and was let to air dry (45° C. minimum of 20 hrs) and thereafter resuspended in sterile distilled water to a concentration three times higher and 200 µl was transferred to 96-wells micro titre plates.

*Candida* was added to a final concentration of ~$10^4$ cells per well and the micro titre plate was incubated at 37° C. for 24 hrs.

pH for the different additives varied between 3.4±0.2. The pH for broth with additive and extracellular product with additive was always the same.

The test was blinded so that there could be no preconceived opinions colouring the results. The inhibition of *Candida* was evaluated and graduated, by two persons using a template, on a scale from five to zero based on visual observations of turbidity with a calculated mean value being presented. Wells containing strong growth of *Candida* in pure dMRSs-broth was graduated as five, while wells with no visual growth were graduated as zero.

Results

As can be seen in FIG. 1 very few additives themselves proved to have an effect on the growth of *Candida* although the pH was very low. The extracellular product of LB 931 was effective in the inhibition of *Candida*. This effect was surprisingly enhanced by the addition of the additives to the extracellular products of LB 931. For all additives in combination with the extracellular product of LB931, a very good growth inhibiting effect was achieved. The best effect was achieved when propionic acid was added to the extracellular product of LB931 (no growth at all).

Test 2

The purpose of these tests was to determine whether selected additives affect the growth of bacteria and if an improved growth inhibition can be achieved when they are added to the extracellular products of *Lactobacillus plantarum*, LB 931. The additives used in this test were sodium acetate, succinic acid, sodium propionate, acetic acid.

Method

Bacterial Strains

Clinical isolates of *E. coli* (designated *E. coli* 1) and *Staphylococcus saprophyticus* (*S. saprophyticus* 1) were used as test strains. They were isolated from the genital tract in women with urinary tract infections.

Control

As a control pure dM17s broth (M17 broth modified by addition of $MnSO_4$ (final conc. 0.04 g/l), $MgSO_4$ (final conc. 0.2 g/l) and glucose (final conc. 20 g/l) was used. 200 µl was added to 96-wells micro titre plates.

Extracellular Product (ECP)

Cultures of LB 931 grown in dM17s broth were centrifuged to pellet the cells and sterile filtered using a 0,22 µm filter (MILLIPORE filter, Bedford, USA) in order to obtain the LB 931 supernatant comprising the LB 931 extracellular product. 200 µl were transferred to 96-wells micro titre plates.

Extracellular Product with Additive

The additives were added to a final concentration of 50 mM to tubes containing the sterile filtered suspension of LB 931. 200 µl was transferred to 96-wells micro titre plates.

Broth with Additive

The additives were added to a final concentration of 50 mM in dM17s broth. 200 µl were added to 96-wells micro titre plates.

10 µl of an over-night culture of *E. coli* resp. *S. saprophyticus*, both diluted 100×, were added to the wells in the micro titre plate which was incubated in 37° C. over night.

pH was adjusted to 6.9 in all trials.

The test was blinded so that there could be no preconceived opinions colouring the results. The inhibition of *E. coli* resp. *S. saprophyticus* was evaluated and graduated, by two persons using a template, on a scale from five to zero based on visual observations of turbidity with a calculated mean value being presented. Wells containing strong growth of *E. coli* resp. *S. saprophyticus* in pure dM17s-broth was graduated as five, while wells with no visual growth were graduated as zero.

Results

Figure 2A:
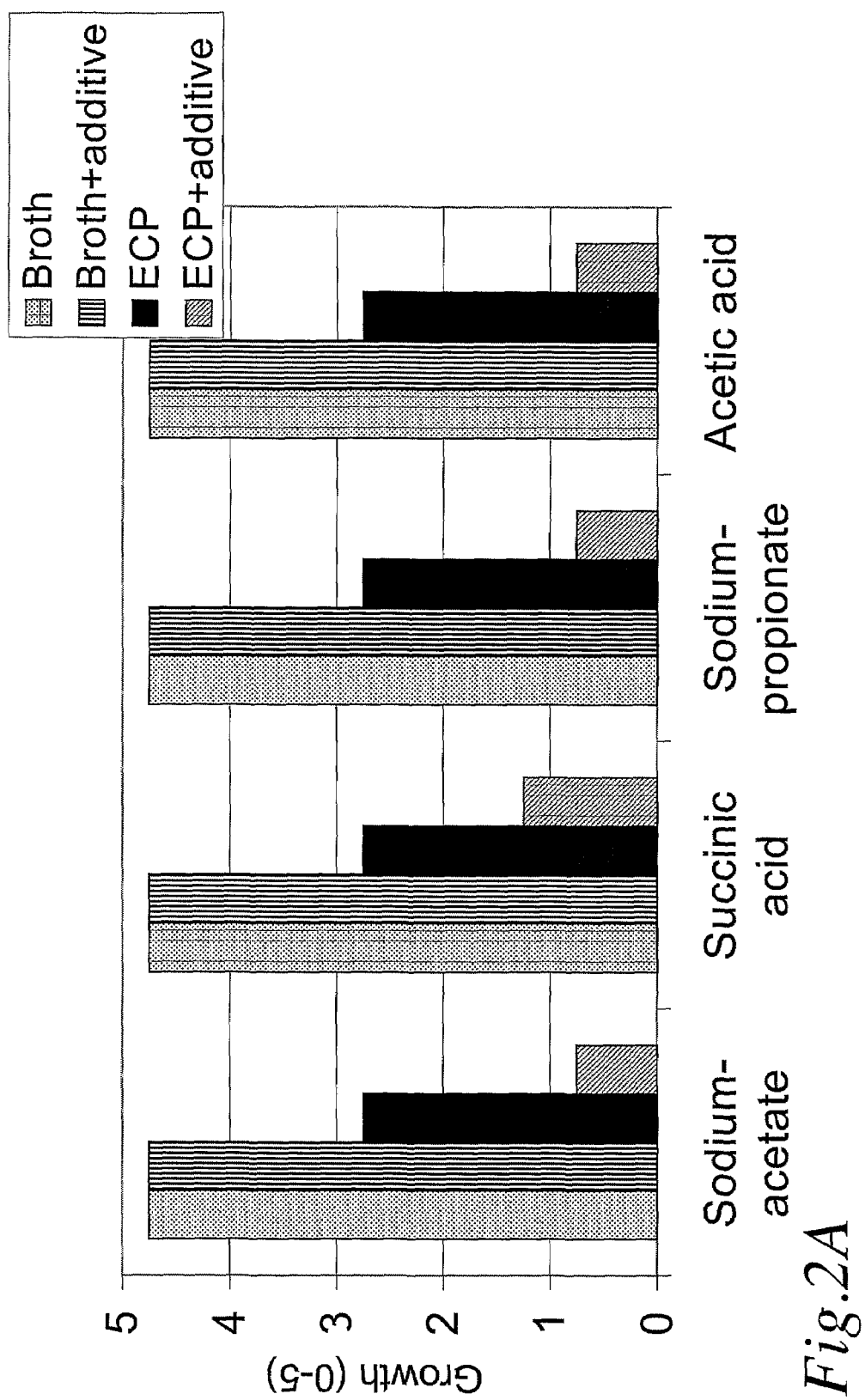
FIG. 2a. shows the growth of *E. coli* in extracellular product of LB 931 with addition (50 mM) of different acids/salts.

As can be seen in FIG. 2A none of the tested additives alone proved to have an effect on the growth of *E. coli*. The extracellular product of LB 931 was effective in the inhibition of *E. coli*. This effect was surprisingly enhanced by the addition of the additives to the extracellular products of LB 931. For all additives in combination with the extracellular product of LB931, a very good growth inhibiting effect was achieved.

Figure 2B:
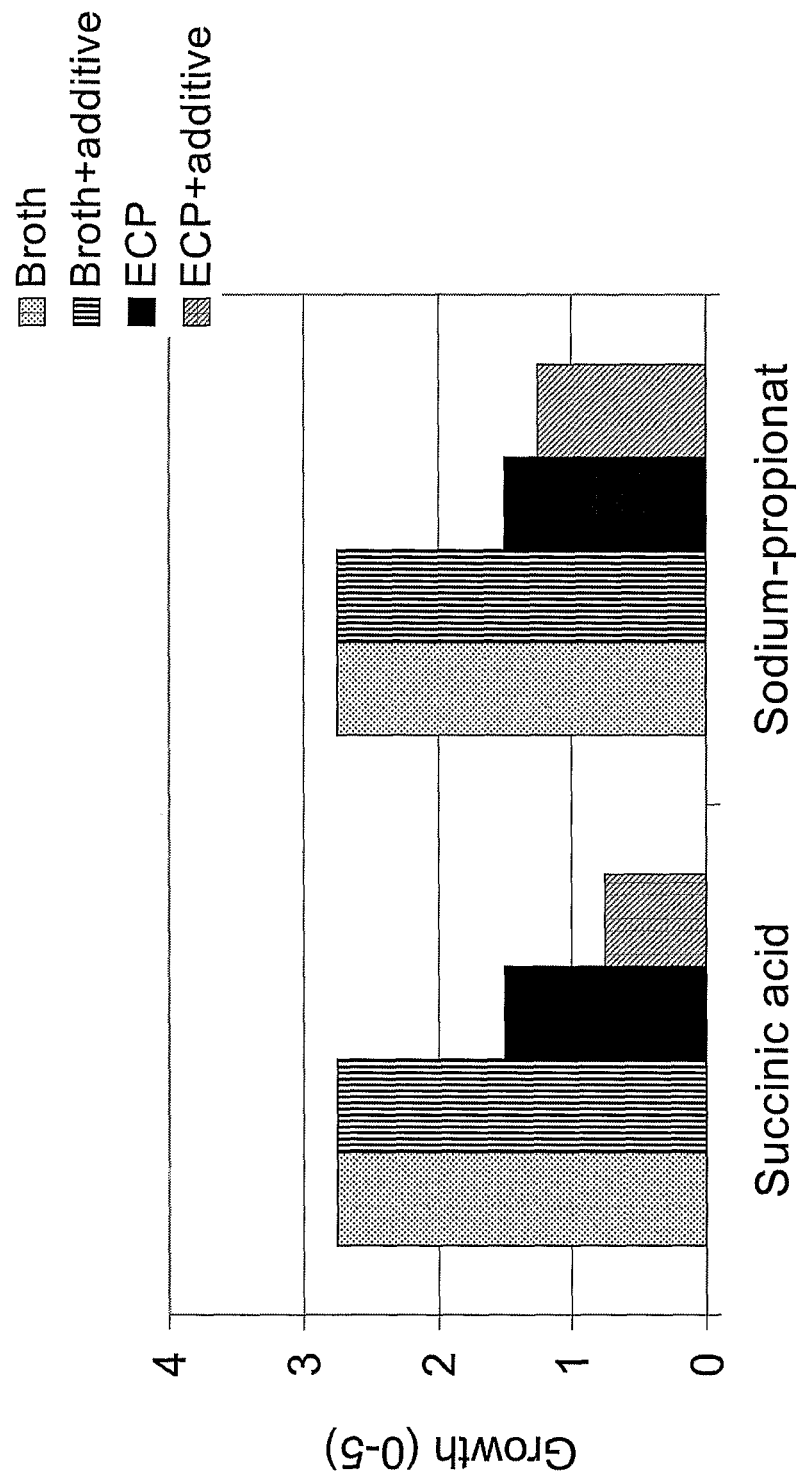
FIG. 2b. shows the growth of *S. Saprofyticus* in extracellular product of LB 931 with addition (50 mM) of different acids/salts.

As can be seen in FIG. 2B none of the tested additives alone proved to have an effect on the growth of *Staphylococcus saprophyticus*. The extracellular product of LB 931 was effective in the inhibition of *Staphylococcus saprophyticus*. This effect was surprisingly enhanced by the addition of the additives to the extracellular products of LB 931. For all additives in combination with the extracellular product of LB 931, a very good growth inhibiting effect was achieved.

Test 3

The purpose of this test was to evaluate the enhanced inhibition of *Candida albicans* when extracellular product of the *Lactobacillus fermentum* Ess-1 was combined with the additives ascorbic acid or propionic acid.

Method

Ess-1 was grown to stationary phase in dMRSs broth (MRS broth without addition of sodium acetate). The bacterial culture was centrifuged to pellet the cells and sterile filtered using a 0,22 μm filter (MILLIPORE filter, Bedford, USA) whereupon the supernatant comprising the extracellular product was obtained. Propionic acid and ascorbic acid were added to a final concentration of 50 mM to tubes containing the extracellular product. The filtrate was pH adjusted to the pKa-value for respective acid (4,2 for ascorbic acid and 4,87 for propionic acid) and 200 μl were transferred to wells of a 96-wells micro titre plate. *C. albicans* was added to a final concentration of ~$5 \times 10^4$ CFU m$l^{-1}$ to each wells. The plates were incubated for 20 hours at 37° C. and the growth was evaluated and graduated, by two persons using a template, on a scale from five to zero based on visual observations of turbidity with a calculated mean value being presented. Wells containing strong growth of *Candida* in pure dMRSs-broth was graduated as five, while wells with no visual growth were graduated as zero.

Results

Figure 3B:
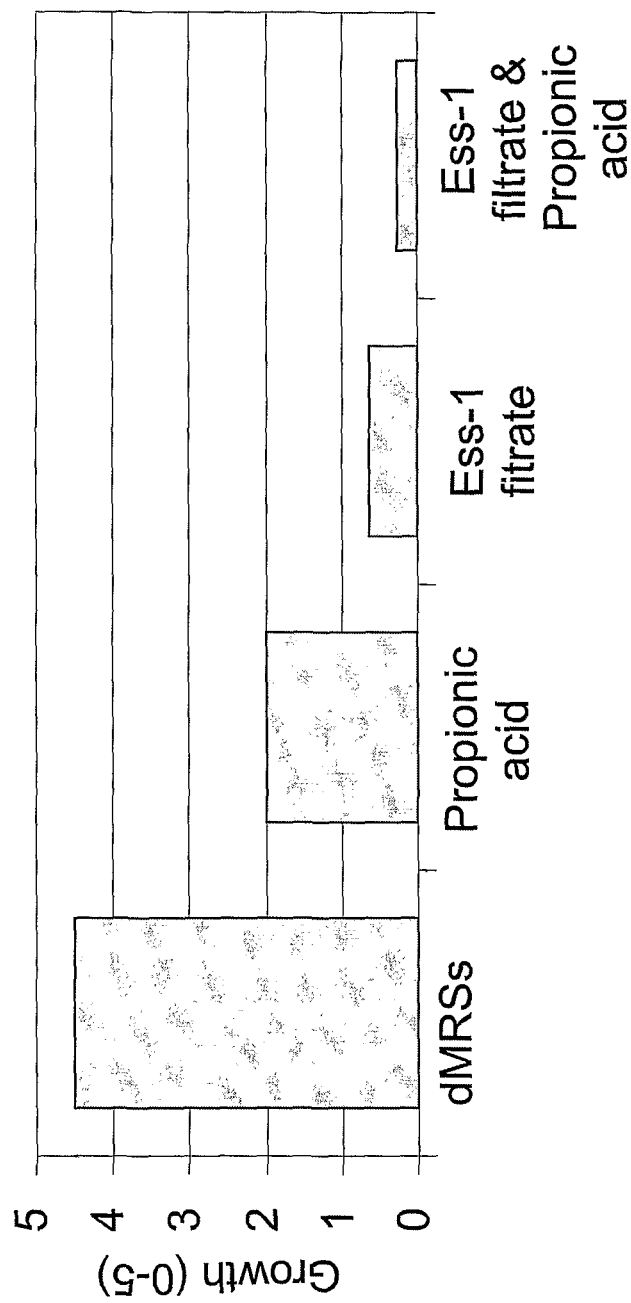
FIG. 3b. shows the growth of *Candida albicans* when extracellular product of the *Lactobacillus fermentum* Ess-1 was combined with the additive propionic acid.

An unexpected increased inhibition was obtained when the supernatant from Ess-1 was combined with either ascorbic acid or propionic acid as can be seen in FIGS. 3A and 3B respectively.

Test 4

The purpose of this test was to evaluate the enhanced *Candida* inhibition from Na-acetate in combination with growing cells of *Lactobacillus plantarum* LB 931.

Method

Two plates were made with M17 agar and two with MRS agar. MRS medium (developed by De Man, Rogosa and Sharpe), is a growth medium commonly used for *Lactobacillus*. MRS agar from Merck contains 5 g sodium acetate per litre agar. M17 (Oxoid) is a similar commercial substrate for *Lactobacillus* but without the addition of sodium acetate. The agars were prepared as described on the packages.

*Lactobacillus plantarum* LB931 was cultivated in MRS broth in 37° C. with 5% $CO_2$ for 24 hours. *Candida albicans* 702 was cultivated in M17 broth at 37° C. for 24 hours.

Holes (Ø 10 mm) were punched in the plates and filled with 250 μl plugs of agar mixtures containing ~$10^7$ LB 931 in MRS agar). The plates were left for 30 minutes and then incubated 24 hours at 37° C. with 5% $CO_2$. Overnight culture of *C. albicans* in M17 broth was diluted 10 times and 100 μl was spread on the surface of each plate. The plates were then incubated for 24 hours at 37° C. As controls, holes (Ø 10 mm) were filled with only MRS agar.

The plates were evaluated in respect to *Candida* growth inhibition. Zones around the plugs with no growth of *Candida* were measured (Ø mm).

Results

The sizes of the zones can be seen in Table 1

TABLE 1

| Agar in the Petri dish | Plug with only agar (Ø mm) | Plug with LB931 (Ø mm) |
|---|---|---|
| MRS agar | 0 | 18.8 |
| M17 agar | 0 | 0 |
| MRS agar | 0 | 18.1 |
| M17 agar | 0 | 0 |

LB 931 grew well in all plugs where LB 931 had been inoculated. There were no zones without growth of *Candida* on the plates with M17 agar. On the MRS agar plates there were clear zones around the LB 931 plugs but no zones around the plugs with only agar.

LB 931 was applied in quite low amounts to the plates, which may explain why substantially no inhibition of *Candida* was seen on the M17 agar plates. This however indicates the efficient inhibition of *Candida* due to the synergistic effect of LB 931 and the additive, in this case sodium acetate comprised in the MRS medium.

EXAMPLES

The following examples related to this invention are illustrative and should not, of course, be construed as specifically limiting the invention.

Example 1

Isolation and Typing of Ess-1

The initial purpose of this study is to isolate and type a *Lactobacillus* strain that inhibit the growth of *Candida albicans* and *Candida glabrata* to a large extent compared to other *Lactobacillus* strains.

Method

Yeast Strains

Clinical isolates of *Candida albicans* and *Candida glabrata* were used as test strains. These were isolated from the vagina of women with vaginal candidiasis and from healthy females.

Screening I.

About 140 *Lactobacillus* strains, originating from human skin, throat, teeth, baby faeces, vegetables and seeds were cultured in MRS broth and stamped onto MRS agar plates. The agar plates were incubated under anaerobic conditions at 37° C. Additionally, SAB (Sabouraud) agar (LAB M, Bury, UK) was poured onto the MRS agar and was allowed to congeal. *C. albicans* culture was seeded onto the agar and the plates were incubated aerobically at 37° C. A visual evaluation of the inhibition was done. Strains inhibiting *C. albicans* equally or to a greater extent than the reference strain *Lactobacillus plantarum* LB931 were selected for further screening (screening II).

Screening II.

Suspensions of lactobacilli grown in dMRSs broth (MRS broth without addition of sodium acetate) were centrifuged and sterile filtered. The filtrate is henceforth called *Lactobacillus* Cell-free Filtrate, LCF. A specified volume was transferred to wells of a micro titre plate and was let to air dry and thereafter resuspended in sterile distilled water to a concentration three times higher and transferred to 96-wells micro titre plates. *Candida* was added to all vials (three isolates of *C. albicans* and *C. glabrata*, respectively, were used). The inhibition was evaluated by visual observation of turbidity and graduated by two persons using a template on a scale from five to zero. The wells containing strong growth of *Candida* sp. in pure dMRSs-broth was graduated as five, while wells with no visual growth were graduated as zero.

API Typing and Genetic Typing

Identification to the species level was done using the API 50 CHL system (BIOMERIEUX, France), following the manufacturer's instructions. Data from the fermentation tests were analysed using API Lab Plus software. Genetic typing was done by DSMZ (Deutsche Sammiung von Microorganismen and Zellkulturen GmbH) by partial sequence analysis of the 16S rRNA.

Results

All strains were evaluated according to the growth inhibition capacity against *C. albicans* in screening I. 23 *Lactobacillus* strains with results comparable or exceeding the one for LB931 were selected for screening II. Out of those 23 *Lactobacillus* strains, three were reference strains and a majority of the strains had been isolated from the oral tract.

Ess-1 proved to have a comprehensive capacity to inhibit growth of *Candida*. No one of the tested *Lactobacillus* strains was similar to the activity of Ess-1 regarding the effect on both *C. albicans* and *C. glabrata*. The carbohydrate fermentation pattern and the genetic typing for Ess-1 showed that it belongs to the *Lactobacillus fermentum* species.

Characterization of Ess-1

16S rDNA from strain Ess-1 (DSM 17851) was analysed by DSMZ (Deutsche Sammlung von Mikroorganismen und Zellkulturen GmbH) by direct sequencing of about 450 nucleotides of PCR-amplified 16S rDNA. Genomic DNA extraction, PCR mediated amplification of the 16S rDNA and purification of the PCR product was carried our as previously described (Rainey, F. A. et al. Int. J. Sys. Bacteriol. 1996(46): 1088-1092). Purified PCR products were sequenced using the CEQ™DTCS-Quickstart Kit (Beckamn Coulter) following the manufacturers instructions. Sequence reaction products were electrophoresed using the CEQ™8000 Genetic Analysis System.

The resulting sequence data was put into the alignment editor ae2 (Maidak, B. L. et al. Nucl. Acids Res. 1999(27): 171-173), aligned manually and compared with representative 16S rRNA gene sequences of organism belonging to the *Firmicutes* (Maidak, B. L. et al.). For comparison 16S rRNA sequences were obtained from the EMBL data base or RDP (Maidak, B. L. et al.).

As a result of this analysis the following table 2 lists those organisms, whose 16S rRNA gene sequences show the highest similarity values compared to the 16S rDNA sequence of Ess-1.

TABLE 2

| Strain | % 16S rRNA gene sequence similarity to Ess-1 |
| --- | --- |
| Lactobacillus fermentum ATCC 14931 | 99.3 |
| Lactobacillus fermentum KRM | 99.0 |
| Lactobacillus malefermentans DSM 5705 | 85.5 |
| Lactobacillus rossiae ATCC BAA-822 | 88.9 |
| Lactobacillus suebicus DSM 5007 | 86.9 |
| Lactobacillus vaccinostercus DSM 20634 | 87.2 |

The partial 16S rDNA gene sequence of strain Ess-1 shows highest similarity to *Lactobacillus fermentum*. Consequently strain Ess-1 may represent a strain of *Lactobacillus fermentum*, but may as well represent a new species within the genus *Lactobacillus*.

Example 2

Production of Probiotic *Lactobacillus*

In laboratory scale: a sterile vessel with ex. MRS broth is inoculated with a pure inoculate of the desired *lactobacillus* strain. Broth with bacteria is incubated over night in 37° C. and preferably with an atmosphere of 5% $CO_2$. Cells may then be washed using centrifugation and sterile saline. Protective sugar, starch or proteins may be added and the cellmass freeze-dried and milled.

In production scale, the working sead lot is fermented in different steps up to production scale. The production is controlled and optimised for the specific strain to be produced. After fermentation the culture is washed and/or only concentrated using cross-flow microfiltration or centrifugation. Protective substances according to the above are added and the cells can be freeze-dried and milled or spray-dried.

Example 3

Production of Extracellular Product from e.g. *Lactobacillus*

In laboratory scale the overnight culture of the probiotic strain is produced as in Example 2. After filtration or centrifugation the supernatant is collected. The supernatant may be concentrated by evaporation or completely dried for ex. convective drying in dry air, freeze, drying or spray-drying.

In production scale the bacterial culture is fermented in accordance with Example 2. The extracellular product is obtained as a filtrate using cross-flow micro filtration or a supernatant using centrifugation. Also in this case it may be further concentrated using evaporation or completely dry using for eg. spray-drying.

Example 3

Formulations

Hygiene Tissue for Improved Genital Hygiene

Overnight cultures of LB931 and Ess-1 cells with extracellular products in the form of supernatants from both Ess-1 and LB931 were mixed with acetic acid to a final concentration of 50 mM. pH was adjusted to 4,9. The mixture was freeze dried with trehalose and grounded until a powder of fine grains was formed. 10 grams of the powder was added to 120 ml olive oil (FILIPPO BERIO extra virgin olive oil) and shaken until a homogenous solution was formed. An additional aliquot of 80 ml of olive oil was added and the resulting 200 ml solution was vortexed for ca 2 min. The bacterial suspens ion was kept at room temperature for 3 hours, with mixing twice an hour. Tissue sheets (Spun Lace DUPONT) were cut to 6×8 cm squares and placed in sterile stainless steel trays. On each tissue sheet, 4 ml of bacterial suspension was dropped over the tissue to cover it. The tissue sheet was folded in the middle, then from the long side to the middle again and packed in foil bags, which edges were welded.

It should be noted that even if all three examples on formulations only comprise *Lactobacillus plantarum* LB 931 and/or *Lactobacillus fermentum* Ess-1 as probiotic bacteria, all probiotic bacteria suitable for the present invention as previously described may as well be used.

The invention claimed is:

1. A hygiene tissue comprising a microbe-inhibiting composition, said microbe-inhibiting composition comprising an extracellular product of at least one probiotic bacterium and at least one additive in the form of an organic acid, having a pKa value not exceeding 5.5, or a salt thereof, wherein said probiotic bacterium is a lactic acid producing bacterium of *Lactobacillus plantarum* LB 931 or *Lactobacillus fermentum* Ess-1 or a combination thereof, wherein said additive is selected from the group consisting of propionic acid, ascorbic acid, phenylalanine, citric acid, butyric acid, valeric acid, capronic acid, succinic acid, and salts of ascorbic acid, phenylalanine, butyric acid, valeric acid, capronic acid and succinic acid, and
wherein said microbe-inhibiting composition is prepared by adding 5-50 mM additive to said extracellular product, wherein said extracellular product is in the form of a supernatant, obtained by filtration or centrifugation of a culture of the probiotic bacterium.

2. The hygiene tissue according to claim 1, wherein said microbe-inhibiting composition is substantially free from lactic acid producing bacteria.

3. The hygiene tissue according to claim 2, wherein the microbe-inhibiting composition comprises not higher than 10 CFU/ml of lactic acid producing bacteria.

4. The hygiene tissue according to claim 1, wherein said microbe-inhibiting composition further comprises a probiotic bacterium.

5. The hygiene tissue according to claim 1, wherein said additive is a sodium salt of ascorbic acid, phenylalanine, butyric acid, valeric acid, capronic acid or succinic acid.

6. The hygiene tissue according to claim 1, wherein the hygiene tissue is a wet wipe, washcloth, patch, towelette, or napkin.

7. The hygiene tissue according to claim 1, wherein the additive is selected from the group consisting of ascorbic acid, propionic acid, succinic acid, and salts of ascorbic acid and succinic acid.

8. A method of preparing a hygiene tissue according to claim 1, comprising applying said microbe-inhibiting composition to said hygiene tissue.

9. A kit comprising a microbe-inhibiting composition comprising an extracellular product of at least one probiotic bacterium and at least one additive in the form of an organic acid, having a pKa value not exceeding 5.5, or a salt thereof and a hygiene tissue, said microbe-inhibiting composition being provided in an ampoule, a bottle, a tube, or a roll-on device, or as a stick or a spray,
wherein said probiotic bacterium is a lactic acid producing bacterium of *Lactobacillus plantarum* LB 931 or *Lactobacillus fermentum* Ess-1 or a combination thereof,
wherein said additive is selected from the group consisting of propionic acid, ascorbic acid, phenylalanine, citric acid, butyric acid, valeric acid, capronic acid, succinic acid, and salts of ascorbic acid, phenylalanine, butyric acid, valeric acid, capronic acid and succinic acid, and
wherein said microbe-inhibiting composition is prepared by adding 5-50 mM additive to said extracellular product, wherein said extracellular product is in the form of a supernatant, obtained by filtration or centrifugation of a culture of the probiotic bacterium.

10. A kit comprising the hygiene tissue as defined in claim 1 and an absorbent article.

11. The kit comprising the hygiene tissue according to claim 10, wherein the absorbent article is a sanitary napkin, a panty liner, an incontinence protector, a diaper, an incontinence pad, a feminine insert, or a tampon.

* * * * *